Sept. 10, 1974 A. W. FISCHER Plant Pat. 3,614
AFRICAN VIOLET
Filed May 3, 1973
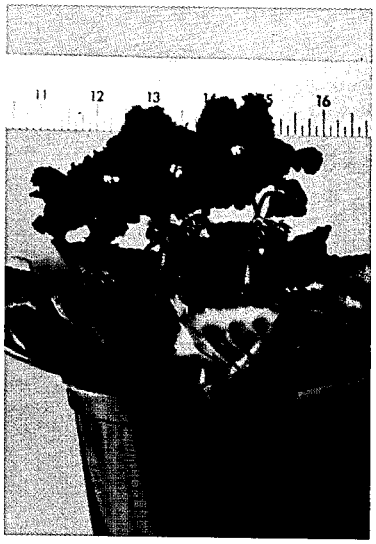
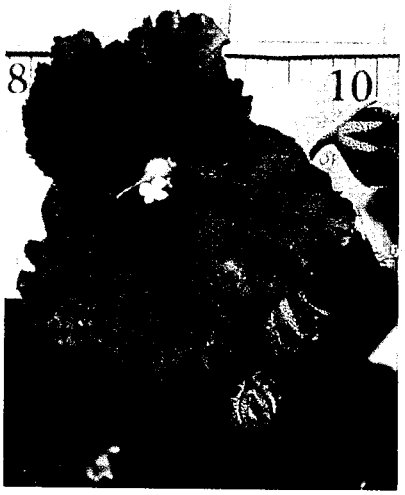
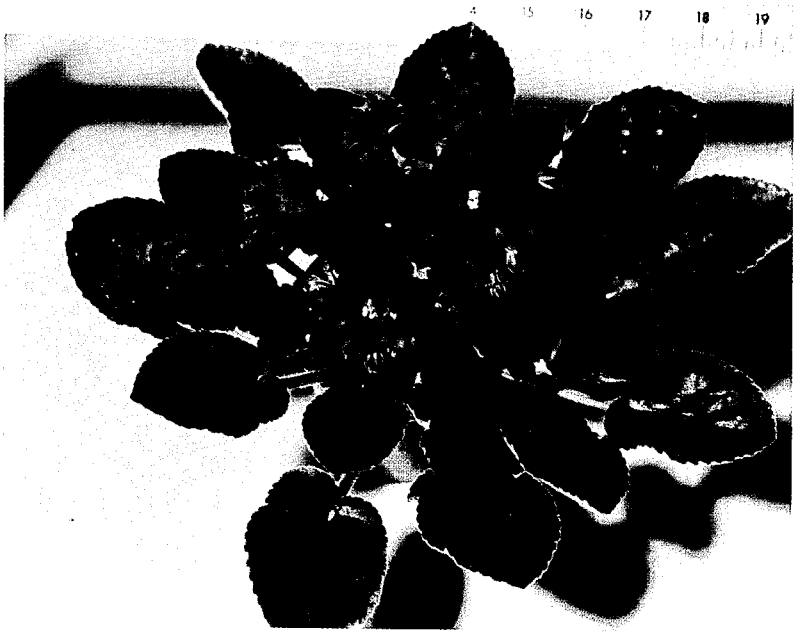

United States Patent Office

Plant Pat. 3,614

Patented Sept. 10, 1974

3,614

AFRICAN VIOLET

Arnold W. Fischer, Isernhagen, Germany, assignor to Geo. J. Ball, Inc., West Chicago, Ill.

Filed May 3, 1973, Ser. No. 357,077

Int. Cl. A01h *5/00*

U.S. Cl. Plt.—69 1 Claim

ABSTRACT OF THE DISCLOSURE

A distinct and new variety of African violet plant distinguished by its large upstanding flowers of intense blue color, with petals having wavy and frilled margins, which form a distinctive cluster at the center of the plant rising above a generally horizontal and rotate spread of large leaves having relatively long petioles.

Background of the New Plant Variety

This new variety of African violet plant was originated as a seedling produced by my crossing two African violet varieties selected from among my breeding stock at Isernhagen, Germany, with the objective of developing different and improved varieties suitable for the commercial market. The unusual and distinctive flower appearing on this plant and the unique, generally horizontal spread of its foliage caused me to select this plant for propagation and test. My asexual reproduction of this plant through several generations as Isernhagen, Germany, by means of leaf cuttings, demonstrated that these unusual characteristics were firmly fixed, where upon commerical propagation by leaf cuttings and division of shoots was begun and is now carried on at West Chicago, Ill., U.S.A., the distinctive features of the new plant holding true from generation to generation.

Description of the Drawing

The new variety of African violet plant is illustrated by the accompanying drawing which shows the form, growth habit, and color characteristics of the plant, the color reproduction being as nearly true as is reasonably possible to be had by conventional photographic procedures. The left-hand upper view shows the manner with which the flowers stand above the horizontally spreading foliage; the right-hand upper view is a close-up of a fully opened blossom of the new plant; and the lower view is taken downwardly from above the plant to show the foliage spread.

The color patches A and B, applied to the drawing, are painted to show the true colors of the top sides and reverse sides, respectively, of the flower petals.

Description of the New Plant

The following is a detailed description of the new variety of African violet plant with color designations according to the Horticultural Colour Chart (HCC) produced by Robert F. Wilson for the British Colour Council and published by The Royal Horticultural Society at London, England.

THE PLANT

Origin: Seedling.

Parentage:

*Seed Parent.*—#65–1, an unnamed and unpatented variety in my breeding stock.

*Pollen Parent.*—#X69–24, an unnamed and unpatented variety in my breeding stock.

Classification:

*Botanic.*—*Saintpaulia ionantha.*

*Commercial.*—Potted African violet.

Form: Compact potted plant.

Height: About 3½ inches from base (soil) to top of flowers.

Growth: Vigorous and condensed with strong petioles which spread horizontally in rotate fashion to hold the leaves slightly inclined upwardly so that they do not hang over the edge of the pot.

Foliage: Quantity—Abundant.

*Size of Leaf.*—3 inches long and 2½ inches wide, in the mature leaf.

*Shape of Leaf.*—Ovate with crenate margins.

*Texture.*—Tomentose.

*Veins.*—Pinnate—very pronounced on under side of leaf.

*Color.*—Upper side—Ivy Green 0001060. Under side—Maroon 1030/3 on younger leaves and near midrib on older leaves. Veronese Green 660/2 on outer margins of older leaves.

*Petioles.*—3 inches or more on mature leaf.

THE BUD

Form: Globular, becoming urn-shaped as it opens.

Size: ⅜ inch diameter, just before opening.

Opening Rate: Very slow—five weeks from visible bud to opening of flower.

Color: Campanula Violet 37/1 when petals begin to unfurl.

Sepals: Hooded over bud for very short period. Sepals stand up upon opening.

*Form.*—Spear-shaped and unbranched.

*Color.*—Inside—Pea Green 61/2. Outside—Maroon 1030.

Calyx: Funnel-shaped and synsepalous.

*Splitting.*—Calyx splits to star shape.

*Aspect.*—Smooth on inside. Hairy on outside.

Peduncle: 2½ inches long, erect, and of tomentose aspect.

*Color.*—Maroon 1030.

THE FLOWER

Blooming Habit: Profuse and recurrent the year around.

Size: Large. About 2½ inches in diameter.

Shape: Very open cup-shaped when first opening becoming almost flat as bloom matures.

Borne: The inflorescence is a cyme.

Petalage: Number—Five, with three larger than remaining two.

*Arrangement.*—Sympetalous.

*Form.*—Orbiculate with bilateral symmetry and frilled undulated margins.

*Color.*—Top side—Victoria Violet 738. Reverse side—Campanula Violet 37/1.

*Texture.*—Leathery. Appearance: Velvety.

Peduncle: Studry, upright, about 2½ inches long.

*Pedicels.*—About 1 inch long.

*Color.*—Maroon 1030.

Effect of Weather: Hot weather suppresses flowering and fades the color. The plant thrives in 80% to 90% humidity.

Fragrance: None.

Lasting Quality: 10 to 14 days for the fully opened flower.

Persistence: Flowers hang on and dry. Petals do not drop.

REPRODUCTIVE ORGANS

Stamens:

*Anthers.*—Two in number, each composed of two anther cells, basifixed in arrangement, and about 1/16 inch long.

*Filaments.*—Length—About ⅛ inch. Color: Victoria Violet 738/2.

*Pollen.*—Color—White.

Pistils: One. Style—5/16 inch long.

*Stigma.*—Victoria Violet 738 in color.

*Ovaries.*—Tomentose and superior.

This new variety of African violet plant is particularly attractive as a house plant. It is vigorous in growth habit producing abundant foliage, which spreads outwardly in rotate fashion, and large frilled blossoms of intense blue color which form a distinctive upstanding cluster at the center of the plant. The profuse and year around recurrent blooming habit of this new variety also adds to its overall attractiveness and commercial value.

I claim:

1. A new variety of African violet plant, substantially as herein shown and described, characterized by the intense blue color of its relatively large flowers which rise upwardly in a central cluster above a rotate, generally horizontal spread of large leaves on strong peduncles which support the leaves in a slightly upward inclined position.

No references cited.

ROBERT E. BAGWILL, Primary Examiner